United States Patent
Herlinger et al.

(10) Patent No.: US 11,666,349 B2
(45) Date of Patent: Jun. 6, 2023

(54) ENDOVASCULAR APPARATUS

(71) Applicant: C. R. Bard, Inc., Franklin Lakes, NJ (US)

(72) Inventors: Nir Herlinger, Scottsdale, AZ (US); Jessica Lynn Roll Hoye, Phoenix, AZ (US); Kevin Hugh Vincent Boyle, Scottsdale, AZ (US)

(73) Assignee: C.R. Bard, Inc., Franklin Lakes, NJ (US)

( * ) Notice: Subject to any disclaimer, the term of this patent is extended or adjusted under 35 U.S.C. 154(b) by 468 days.

(21) Appl. No.: 16/764,682

(22) PCT Filed: Nov. 30, 2017

(86) PCT No.: PCT/US2017/063830
§ 371 (c)(1),
(2) Date: May 15, 2020

(87) PCT Pub. No.: WO2019/108187
PCT Pub. Date: Jun. 6, 2019

(65) Prior Publication Data
US 2021/0022758 A1 Jan. 28, 2021

(51) Int. Cl.
*A61B 17/00* (2006.01)
*A61B 17/22* (2006.01)
*A61B 17/32* (2006.01)

(52) U.S. Cl.
CPC .............. *A61B 17/2202* (2013.01); *A61B 2017/00336* (2013.01); *A61B 2017/00477* (2013.01);
(Continued)

(58) Field of Classification Search
CPC ............... A61B 17/2202; A61B 17/34; A61B 17/3415; A61B 17/3417; A61B 17/3421;
(Continued)

(56) References Cited

U.S. PATENT DOCUMENTS

| 5,098,412 A | 3/1992 | Shiu |
| 5,454,785 A | 10/1995 | Smith |

(Continued)

FOREIGN PATENT DOCUMENTS

| CA | 2682893 A1 | 10/2008 |
| CN | 1213977 A | 4/1999 |

(Continued)

OTHER PUBLICATIONS

Office Action dated Sep. 30, 2021, pertaining to corresponding Japanese Patent Appln. No. 2020 529594. (English Translation).

(Continued)

*Primary Examiner* — Ryan J. Severson
(74) *Attorney, Agent, or Firm* — Dinsmore & Shohl LLP

(57) ABSTRACT

An endovascular apparatus includes a first cannula, a second cannula, and an operator handle. The first cannula has a proximal end, a distal end, and a first lumen. The second cannula is slidably coupled to the first cannula. The second cannula has a proximal end portion, a distal end portion, and a second lumen. The distal end portion is extendable in a distal direction beyond the distal end of the first cannula. The operator handle is operably coupled to the second cannula. The operator handle may be configured to articulate the distal end portion of the second cannula relative to the first cannula. The second cannula may include an articulation joint. Optionally, the operator handle may be configured to extend, retract, and rotate the second cannula relative to the first cannula. Also, optionally, the endovascular apparatus may include a magnetic coupler.

17 Claims, 4 Drawing Sheets

(52) U.S. Cl.
CPC .............. *A61B 2017/00876* (2013.01); *A61B 2017/320071* (2017.08)

(58) Field of Classification Search
CPC .......... A61B 2017/00336; A61B 2017/00477; A61B 2017/00876; A61B 2017/320071; A61B 2017/3445; A61B 2017/3447
See application file for complete search history.

(56) References Cited

U.S. PATENT DOCUMENTS

| | | | |
|---|---|---|---|
| 5,478,309 A * | 12/1995 | Sweezer | A61M 1/3659 604/6.14 |
| 5,765,568 A * | 6/1998 | Sweezer, Jr. | A61M 60/117 604/509 |
| 5,800,375 A * | 9/1998 | Sweezer | A61M 60/295 604/4.01 |
| 5,810,757 A * | 9/1998 | Sweezer, Jr. | A61M 60/113 604/6.14 |
| 5,921,971 A | 7/1999 | Agro et al. | |
| 6,248,086 B1 * | 6/2001 | Sweezer | A61M 60/113 604/4.01 |
| 6,293,920 B1 | 9/2001 | Sweezer et al. | |
| 6,394,956 B1 | 5/2002 | Chandrasekaran et al. | |
| 6,398,752 B1 * | 6/2002 | Sweezer, Jr. | A61M 25/1011 604/4.01 |
| 6,585,705 B1 | 7/2003 | Maginot et al. | |
| 6,969,379 B1 | 11/2005 | Aboul-hosn et al. | |
| 6,995,832 B2 | 2/2006 | Okuyama | |
| 7,018,374 B2 | 3/2006 | Schon et al. | |
| 7,637,905 B2 * | 12/2009 | Saadat | A61B 1/0055 606/1 |
| 7,740,633 B2 * | 6/2010 | Assell | A61B 17/025 606/96 |
| 7,914,503 B2 | 3/2011 | Goodson, IV et al. | |
| 8,147,427 B2 | 4/2012 | Nanto et al. | |
| 8,425,455 B2 | 4/2013 | Nentwick | |
| 8,500,939 B2 | 8/2013 | Nimkar et al. | |
| 8,562,566 B2 | 10/2013 | Weber | |
| 8,585,950 B2 | 11/2013 | Appling et al. | |
| 8,926,564 B2 | 1/2015 | King et al. | |
| 8,992,454 B2 | 3/2015 | Anand | |
| 9,078,998 B2 | 7/2015 | King | |
| 9,126,013 B2 | 9/2015 | Watanabe | |
| 9,271,787 B2 | 3/2016 | Katoh et al. | |
| 9,278,188 B2 | 3/2016 | King | |
| 9,358,365 B2 | 6/2016 | Smith et al. | |
| 9,561,073 B2 | 2/2017 | Ogata et al. | |
| 9,669,149 B2 | 6/2017 | Anand | |
| 9,717,882 B2 | 8/2017 | Tassoni, Jr. et al. | |
| 2002/0161321 A1 | 10/2002 | Sweezer, Jr. et al. | |
| 2004/0138525 A1 | 7/2004 | Saadat et al. | |
| 2004/0220473 A1 | 11/2004 | Lualdi | |
| 2008/0249483 A1 * | 10/2008 | Slenker | A61M 1/0058 600/101 |
| 2010/0168642 A1 | 7/2010 | Appling et al. | |
| 2011/0276038 A1 | 11/2011 | McIntyre et al. | |
| 2012/0029513 A1 * | 2/2012 | Smith | A61M 25/0054 606/41 |
| 2012/0136341 A1 | 5/2012 | Appling et al. | |
| 2012/0239003 A1 | 9/2012 | Julson et al. | |
| 2013/0172828 A1 | 7/2013 | Kappel et al. | |
| 2013/0253445 A1 | 9/2013 | Nimkar et al. | |
| 2015/0335810 A1 | 11/2015 | Anand | |
| 2016/0051323 A1 | 2/2016 | Stigall et al. | |
| 2017/0042610 A1 * | 2/2017 | Smith | A61M 25/0113 |
| 2017/0143890 A1 | 5/2017 | Nardeo | |
| 2017/0165455 A1 | 6/2017 | Kumagai | |
| 2021/0022758 A1 * | 1/2021 | Herlinger | A61M 25/0133 |

FOREIGN PATENT DOCUMENTS

| | | |
|---|---|---|
| CN | 106028984 A | 10/2016 |
| CN | 107073240 A | 8/2017 |
| EP | 0760688 A1 | 3/1997 |
| JP | 2006-516910 A | 7/2006 |
| KR | 20120089852 A | 8/2012 |
| WO | 2004064600 A2 | 8/2004 |
| WO | 2012051292 A1 | 4/2012 |
| WO | 2015116003 A1 | 8/2015 |
| WO | 2016056100 A1 | 8/2017 |

OTHER PUBLICATIONS

Office Action dated Dec. 1, 2021, pertaining to Chinese Patent Application 201780097293.1 (English Translation).

* cited by examiner

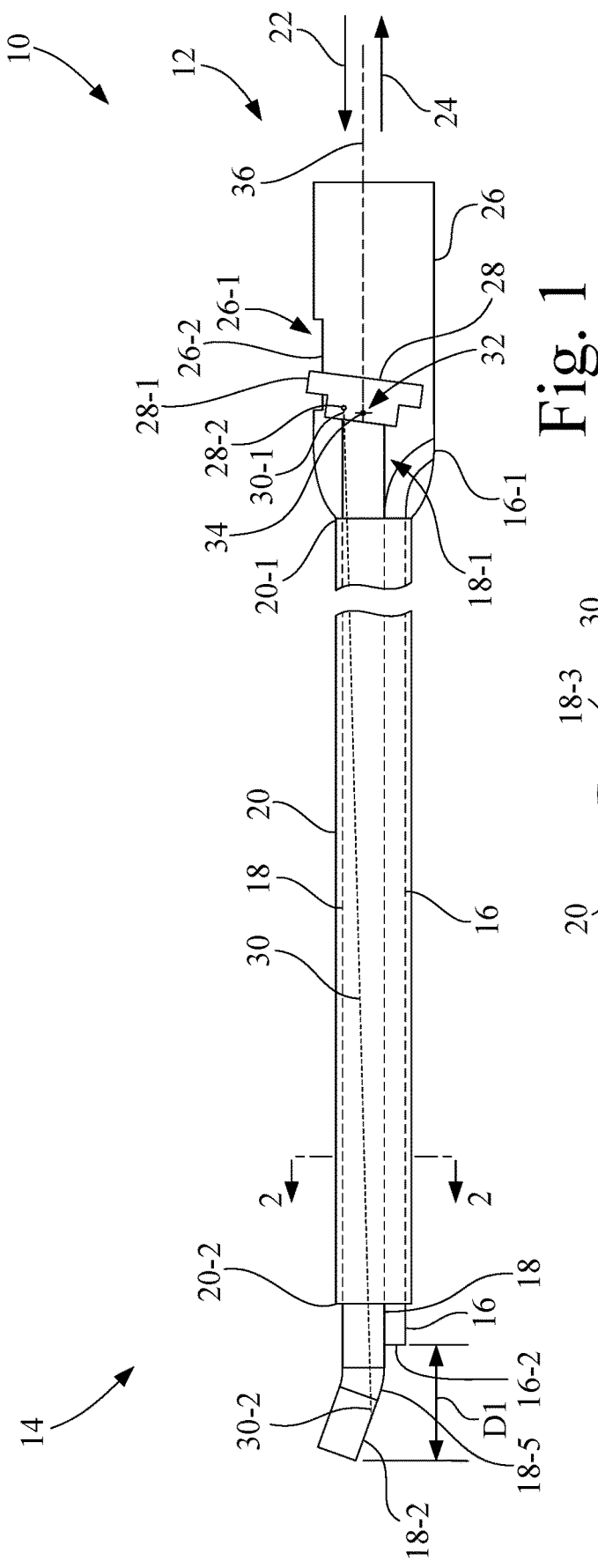

ENDOVASCULAR APPARATUS

CROSS-REFERENCE TO RELATED APPLICATIONS

This application is a U.S. national phase of International Application No. PCT/US2017/063830, filed Nov. 30, 2017, which is incorporated herein by reference in its entirety.

TECHNICAL FIELD

The present invention relates to an endovascular apparatus.

BACKGROUND ART

Efforts continue in the endovascular art to improve the accuracy of placement of devices within a patient in performing invasive procedures and/or to traverse diseased tissue safely.

SUMMARY OF INVENTION

The present invention provides a dual cannula/lumen arrangement for a catheter that has the ability to extend or retract, rotate, and/or articulate one cannula relative to the other cannula and/or the cannula arrangement may be used in conjunction with a guide wire and an intravascular device, wherein the guide wire and an intravascular device are magnetically coupled.

The invention in one form is directed to an endovascular apparatus that includes a first cannula, a second cannula, and an operator handle. The first cannula has a proximal end, a distal end, and a first lumen. The second cannula is slidably coupled to the first cannula. The second cannula has a proximal end portion, a distal end portion, and a second lumen. The distal end portion is extendable in a distal direction beyond the distal end of the first cannula. An operator handle is operably coupled to the second cannula. The operator handle may be configured to articulate the distal end portion of the second cannula relative to the first cannula. The operator handle is for operation by an operator.

The second cannula may include an articulation joint. The operator handle may be configured to extend, retract, and rotate the second cannula relative to the first cannula.

The invention in another form is directed to an endovascular apparatus having a first cannula, a second cannula, a guide wire, an intravascular device, and a magnetic coupler. The guide wire is located in the first lumen of the first cannula. The guide wire is configured to project from the distal end of the first cannula. The intravascular device is received in the second lumen of the second cannula. The intravascular device has a distal working portion that extends distally from the distal end portion of the second cannula. The magnetic coupler is configured to generate a passive magnetic bond between the guide wire and the distal working portion of the intravascular device.

An advantage of some embodiments is that the cannula having the ability to extend or retract, rotate, and articulate may be more precisely positioned within a patient.

Another advantage is that in embodiments that include the guide wire and the intravascular device that are magnetically coupled, the intravascular device tracks the guide wire without separating, such that diseased tissue can be traversed safely.

BRIEF DESCRIPTION OF DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 1 is a side view of an endovascular apparatus that includes an elongate sheath having a sheath lumen that carries a movable cannula and a stationary cannula;

FIG. 2 is a section view of the cannula arrangement of FIG. 1 taken along line 2-2 of FIG. 1;

Corresponding reference characters indicate corresponding parts throughout the several views. The exemplifications set out herein illustrate embodiments of the invention, and such exemplifications are not to be construed as limiting the scope of the invention in any manner.

DESCRIPTION OF EMBODIMENTS

Figure 3A:
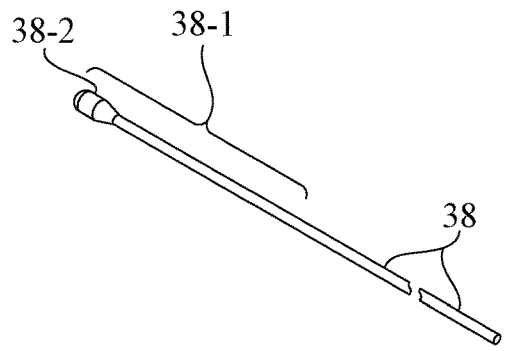
FIG. 3A is a perspective view of an intravascular device that may be inserted into a lumen of the movable cannula, the intravascular device having an attraction member to facilitate magnetic coupling.

Referring now to the drawings, and more particularly to FIGS. 1 and 2, there is shown an endovascular apparatus 10 which generally includes an operator handle 12 and a cannula arrangement 14. Operator handle 12 is operably coupled to cannula arrangement 14. Cannula arrangement 14 includes a first cannula 16, a second cannula 18, and an elongate sheath 20.

First cannula 16 is formed as an elongate tube having a proximal end 16-1, a distal end 16-2, a lumen 16-3, and an exterior surface 16-4. First cannula 16 has a longitudinal extent between the proximal end 16-1 and the distal end 16-2.

Second cannula 18 has a proximal end portion 18-1, a distal end portion 18-2, a lumen 18-3, an exterior surface 18-4, and an articulation joint 18-5. Articulation joint 18-5 is interposed between proximal end portion 18-1 and distal end portion 18-2. Lumen 18-3 extends through each of proximal end portion 18-1, distal end portion 18-2, and articulation joint 18-5.

Articulation joint 18-5 is formed as a flexible tube, and may be formed, for example, from a flexible polymer, such as Pebax® polymer, or as a polymer encased nitinol tube.

Elongate sheath 20 is an elongate tube having a proximal end 20-1, a distal end 20-2, and a sheath lumen 20-3. Elongate sheath 20 is configured to receive both of first cannula 16 and second cannula 18 in sheath lumen 20-3.

In the present embodiment, first cannula 16 and second cannula 18 are positioned in sheath lumen 20-3 of elongate sheath 20, such that second cannula 18 is slidably coupled to first cannula 16. More particularly, second cannula 18 is slidable relative to first cannula 16 within sheath lumen 20-3 of elongate sheath 20. In one implementation, first cannula 16 may be fixedly attached, e.g., by adhesive, to elongate sheath 20 within sheath lumen 20-3 such that first cannula 16 is longitudinally stationary relative to elongate sheath 20, while second cannula 18 remains longitudinally movable within sheath lumen 20-3. In another implementation, each of first cannula 16 and second cannula 18 may be longitudinally and independently movable within sheath lumen 20-3 of elongate sheath 20; in other words, neither first cannula 16 nor second cannula 18 is fixedly attached to elongate sheath 20.

In the present embodiment, exterior surface 18-4 of second cannula 18 is in sliding contact with exterior surface 16-4 of first cannula 16. Distal end portion 18-2 of second cannula 18 is extendable in a distal direction 22 by a distance D1 beyond distal end 16-2 of first cannula 16, i.e., is extendable beyond the longitudinal extent of first cannula 16. Distance D1 is a variable distance, i.e., a distance wherein the distance amount may be selected by the user. In a preferred implementation, both of distal end portion 18-2 and articulation joint 18-5 of second cannula 18 are positioned by the user to extend beyond distal end 16-2 of first cannula 16, such that distal end portion 18-2 of second cannula 18 may be freely articulated relative to first cannula 16 and elongate sheath 20.

In the present embodiment, more particularly, operator handle 12 is operably coupled to the second cannula 18. Operator handle 12 is configured to articulate distal end portion 18-2 of second cannula 18 relative to first cannula 16. Also, operator handle 12 is configured to selectively rotate (clockwise or counterclockwise) second cannula 18 relative to the first cannula 16. In addition, operator handle 12 is configured to selectively move second cannula 18 longitudinally relative to the first cannula 16 in each of a distal direction 22 and in a proximal direction 24. Distal direction 22 and proximal direction 24 are opposite longitudinal directions.

Operator handle 12 includes a housing 26, a hub 28, and a translation member 30. In the present embodiment, housing 26 is transparent to show hub 28 and the connections thereto. Housing 26 is configured as a hollow structure having a cavity 26-1 and a side slot 26-2. Hub 28 is positioned in cavity 26-1 and is pivotably coupled to second cannula 18 via a pivot mechanism 32 at a pivot axis 34. Pivot mechanism 32 may be formed, for example, as a pin/hole arrangement. Hub 28 has an operator lever 28-1 that loosely extends through side slot 26-2, such that hub 28 is rotatably and slidably movable relative to first cannula 16 and housing 26. Hub 28 also has an offset location 28-2 to define a proximal connection location for translation member 30. Offset location 28-2 is laterally offset from pivot axis 34 so as to form a lever advantage.

Translation member 30 is an elongate member, such as a metal or plastic wire, that extends though lumen 18-3 of second cannula 18. Translation member 30 has a proximal end 30-1 and distal end 30-2. Proximal end 30-1 of translation member 30 is connected to hub 28 at offset location 28-2 by a fastener, such as a screw, clamp, weld, adhesive, etc. Distal end 30-2 of translation member 30 is connected to distal end portion 18-2 of second cannula 18 by a fastener, such as a screw, clamp, weld, adhesive, etc.

Hub 28 is axially movable within housing 26 along a rotational axis 36 in distal direction 22 to extend the second cannula 18 relative to the first cannula 16, and hub 28 is axially movable along rotational axis 36 in proximal direction 24 to retract the second cannula 18 relative to the first cannula 16. Hub 28 is rotatable within housing 26 about rotational axis 36 to rotate second cannula 18 within elongate sheath 20 relative to first cannula 16. Also, hub 28 is pivotable within housing 26 about pivot axis 34 to articulate distal end portion 18-2 of the second cannula 18 by exerting a pulling (tension) force on translation member 30 in proximal direction 24 or a pushing force on translation member 30 in distal direction 22, so as to selectively bend distal end portion 18-2 relative to proximal end portion 18-1 at articulation joint 18-5 to achieve the desired angular direction of distal end portion 18-2 relative to proximal end portion 18-1 of second cannula 18.

Alternatively, in embodiments wherein articulation joint 18-5 includes a memory material, such as nitinol, and the relaxed state of articulation joint 18-5 is straight, then translation member 30 need only be capable of applying a pulling (tension) force, and articulation joint 18-5 will return to the relaxed (straight) state when the tension applied by translation member 30 is released. Thus, the amount of angle generated at articulation joint 18-5 is dependent, at least in part, upon the amount of tension applied by translation member 30. Also, since in this implementation translation member 30 need only be capable of applying a pulling (tension) force, translation member 50 may be in the form of a thread, string, or wire.

Accordingly, when distal end portion 18-2 and articulation joint 18-5 are extended in a distal direction 22 beyond the distal end 16-2 of first cannula 16, then second cannula 18 may be articulated at the articulation joint 18-5 by operation of hub 28 of operator handle 12.

Referring to FIGS. 1 and 3A, endovascular apparatus 10 may further include an intravascular device 38, such as a core wire of an ultrasonic device, e.g., an ultrasonic core wire, received in the lumen 18-3 of the second cannula 18. Intravascular device 38 has a distal working portion 38-1 that extends distally from the distal end portion 18-2 of second cannula 18.

Figure 3B:
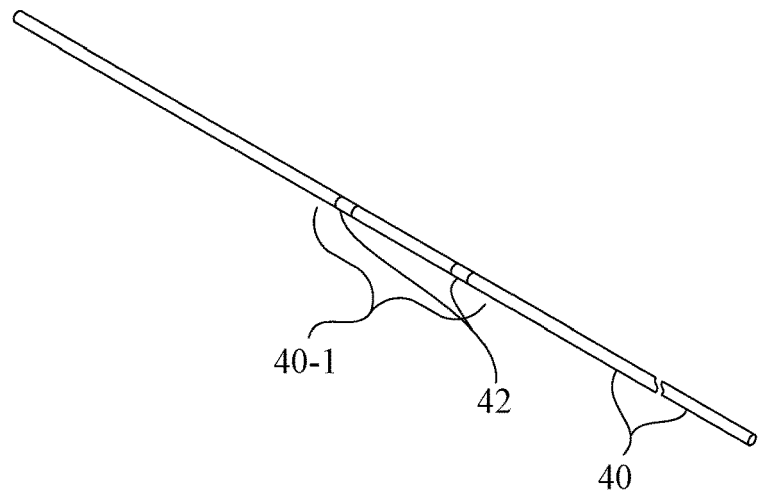
FIG. 3B is a perspective view of a guide wire that may be inserted into a lumen of the stationary cannula, the guide wire having an attraction member section to facilitate magnetic coupling.

Referring to FIGS. 1 and 3B, endovascular apparatus 10 may further include a guide wire 40 that is located in lumen 16-3 of first cannula 16. Guide wire 40 may have a length sufficient such that guide wire 40 projects from each of proximal end 16-1 and distal end 16-2 of first cannula 16.

Figure 4:
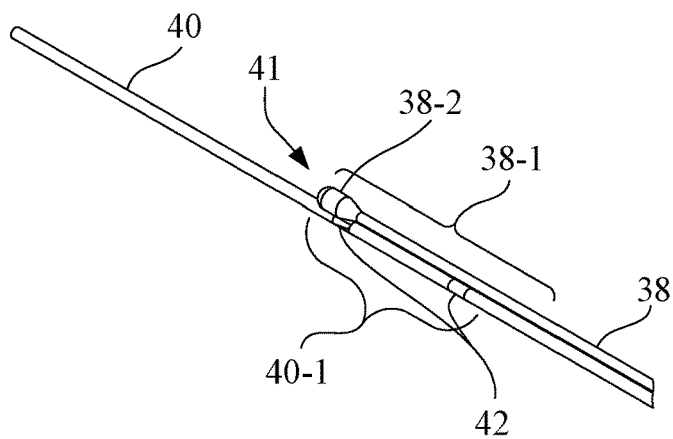
FIG. 4 is a perspective view of the intravascular device and guide wire of FIGS. 3A and 3B, with the intravascular device and the guide wire being magnetically coupled.

Referring also to FIG. 4, intravascular device 38 and guide wire 40 may be configured to form a magnetic coupler 41 that is configured to generate a passive magnetic bond between guide wire 40 and distal working portion 38-1 of intravascular device 38. In embodiments wherein intravascular device 38 is an ultrasonic core wire, intravascular device 38 is configured to be coupled to an ultrasonic energy source to receive an ultrasonic vibrational wave and to transmit the ultrasonic vibrational wave to distal working portion 38-1. The passive magnetic bond between guide wire 40 and distal working portion 38-1 of intravascular device 38 is broken when the ultrasonic vibrational wave (energy) is applied to intravascular device 38 by the ultrasonic energy source. It is contemplated that other types of mechanisms may be used to break the magnetic bond, so long as the mechanism generates a greater force than the attraction force of the selected magnet and ferromagnetic material.

In the embodiment shown in FIGS. 3B and 4, guide wire 40 has an attraction section 40-1 that extends from the distal end 16-2 of the first cannula 16. Also, as shown in FIGS. 3A and 4, distal working portion 38-1 of intravascular device 38 has an attraction member 38-2. Referring to FIG. 4, at least one of attraction section 40-1 of guide wire 40 and attraction member 38-2 of intravascular device 38 has a magnet, e.g., a permanent magnet, to generate a magnetic force to magnetically bond distal working portion 38-1 of intravascular device 38 to attraction section 40-1 of guide wire 40, and the other of attraction section 40-1 of guide wire 40 and attraction member 38-2 of intravascular device 38 is a ferromagnetic material, e.g., an iron alloy or a material that includes iron particles, that is magnetically attracted to the magnet.

Referring again to FIGS. 3B and 4, attraction section 40-1 of guide wire 40 may include a plurality of attraction elements 42 that are spaced along a longitudinal extent of guide wire 40, wherein all of the plurality of attraction elements 42 is a respective magnet or all of the plurality of attraction elements 42 is a respective ferromagnetic material element. Each of the plurality of attraction elements 42 may form an annular band around guide wire 40. It is contemplated that the plurality of attraction elements 42 may also serve as locator markings for identifying a location of guide wire 40 within a patient, or signifying a distance based on the spacing between adjacent pairs of the plurality of attraction elements 42.

Figure 5:
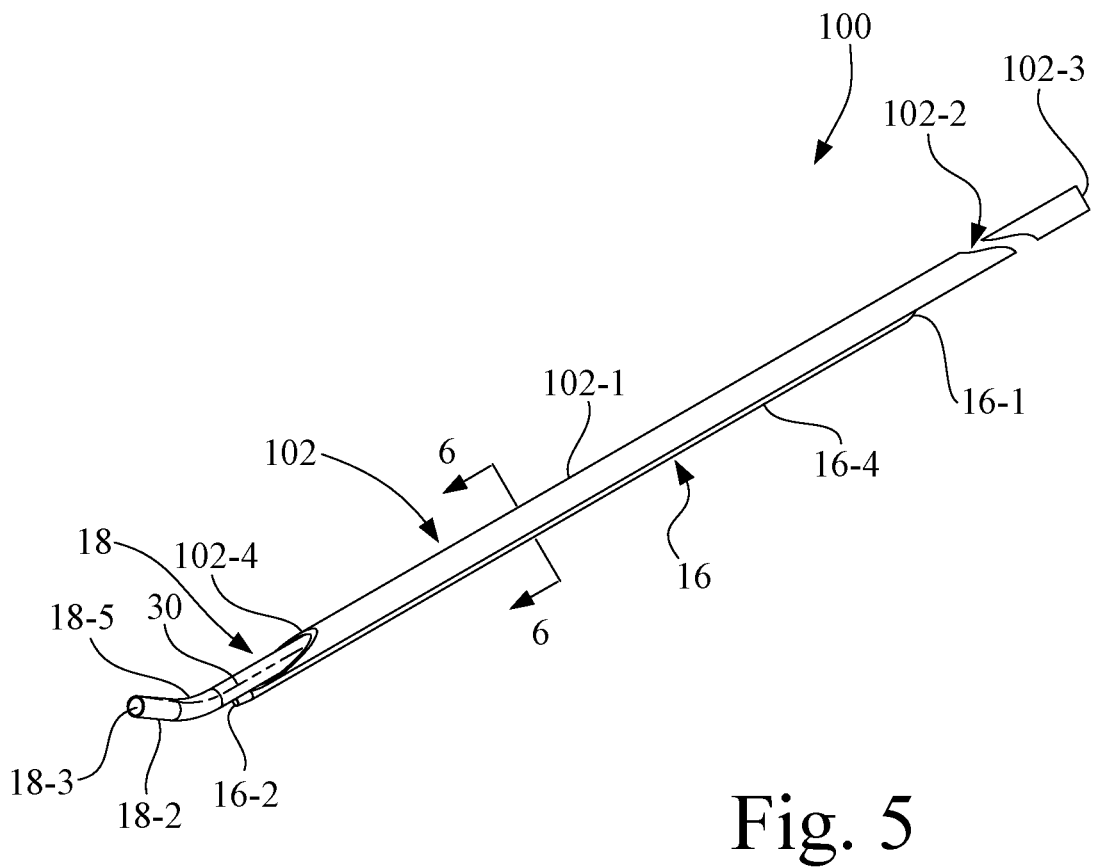
FIG. 5 is a perspective view of an alternative cannula arrangement for use in the endovascular apparatus of FIG. 1, having the stationary cannula attached to an exterior surface of a sheath tube.
Figure 6:
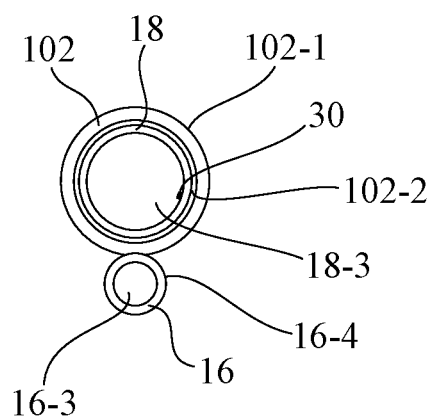
FIG. 6 is a section view of the cannula arrangement of FIG. 5 taken along line 6-6 of FIG. 5.

FIGS. 5 and 6 are directed to another embodiment of a cannula arrangement 100 that may be used as an alternative to cannula arrangement 14 depicted in FIG. 1. Thus, in the discussion that follows, it is to be understood that cannula arrangement 100 replaces cannula arrangement 14 in endovascular apparatus 10 of FIG. 1. Cannula arrangement 100 has a sheath tube 102, first cannula 16, and second cannula 18. Also, FIG. 5 shows a placement of translation member 30, wherein translation member 30 is located inside lumen 18-3 of second cannula 18. It is further contemplated that translation member 30 may be a formed as a plurality of pull wires, e.g., diametrically opposed at distal end portion 18-2, to effect both a bending and straightening of second cannula 18.

Sheath tube 102 has an exterior surface 102-1, a guide lumen 102-2, a proximal end 102-3, and a distal end 102-4. Proximal end 102-3 may be connected to operator handle 12 (see FIG. 1). Distal end 102-4 may be beveled. Exterior surface 102-1 of sheath tube 102 is fixedly attached to exterior surface 16-4 of first cannula 16 along the longitudinal extent of first cannula 16. Second cannula 18 is positioned in guide lumen 102-2 of the sheath tube 102 for slidable movement within the guide lumen 102-2 of sheath tube 102. Distal end portion 18-2 and articulation joint 18-5 of second cannula 18 are extendable in distal direction 22 beyond the distal end 102-3 of sheath tube 102. Second cannula 18 may be articulated at the articulation joint 18-5 by operation of operator handle 12.

Figure 7:
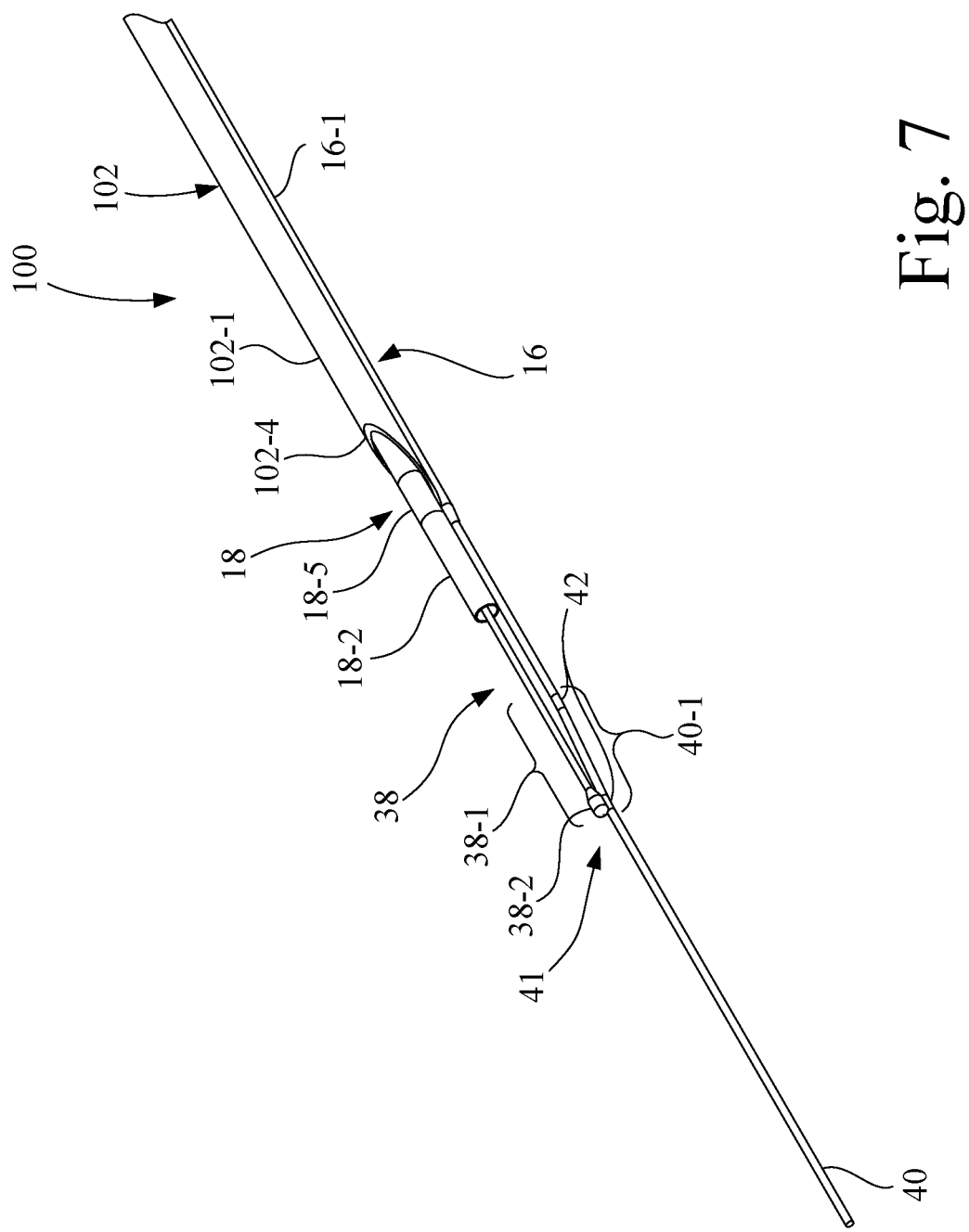
FIG. 7 is a perspective view of the alternative cannula arrangement of FIG. 5, with the intravascular device and guide wire of FIGS. 3A and 3B located in respective lumens and with the intravascular device and the guide wire being magnetically coupled.

Referring to FIG. 7, intravascular device 38 and guide wire 40 may be used with cannula arrangement 100 in the same manner as described above with respect to cannula arrangement 14.

Alternatively, it is to be understood that embodiments that include intravascular device 38 and guide wire 40 may be practiced in the absence of the articulation features of the embodiments described with respect to FIGS. 1-6. Such alternative embodiments are not dependent on a particular cannula arrangement so long as attraction section 40-1 of guide wire 40 and attraction member 38-2 of intravascular device 38 are in proximity such that the magnetic bond may be formed between attraction member 38-2 at distal working portion 38-1 of intravascular device 38 and attraction section 40-1 of guide wire 40.

Also, alternatively, it is contemplated to apply the magnetic coupling principles described above to cannula arrangement 100 of FIG. 5, wherein first cannula 16 and second cannula 18 incorporate magnetic coupler 41. More particularly, magnetic coupler 41 is configured to generate a passive magnetic bond between first cannula 16 and second cannula 18. For example, first cannula 16 may include attraction member 38-2 at distal end 16-2, and second cannula 18 may include an attraction element 42 at distal end portion 18-2. In this configuration, the retractable second cannula 18 may be magnetically coupled to the fixed first cannula 16 when second cannula 18 is retracted to a pre-specific, e.g., zero, position. For example, the user may rotate or extend second cannula 18, but once second cannula 18 is retracted close to the zero position, then second cannula 18 would magnetically snap back to the zero position by the attractive force of the passive magnetic field generated by magnetic coupler 41. This would provide a tactile response to the user that they are at the pre-specified, e.g., zero, position.

The following items also relate to the invention:

In one form, the invention relates to an endovascular apparatus having a first cannula, a second cannula, and an operator handle. The first cannula has a proximal end, a distal end, and a first lumen. The second cannula is slidably coupled to the first cannula. The second cannula has a proximal end portion, a distal end portion, and a second lumen. The distal end portion is extendable in a distal direction beyond the distal end of the first cannula. The operator handle is operably coupled to the second cannula. The operator handle is configured to articulate the distal end portion of the second cannula relative to the first cannula and/or to rotate (clockwise and/or counterclockwise) the second cannula relative to the first cannula and/or to selectively move the second cannula longitudinally relative to the first cannula. The endovascular apparatus is configured to articulate the distal end portion of the second cannula relative to the first cannula and/or to rotate (clockwise and/or counterclockwise) the second cannula relative to the first cannula and/or to selectively move the second cannula longitudinally relative to the first cannula, upon respective operation of the operator handle.

Optionally, the apparatus may include an elongate sheath that has a sheath lumen. Each of the first cannula and the second cannula may be positioned in the sheath lumen of the elongate sheath. The second cannula is slidable relative to the first cannula within the sheath lumen of the elongate sheath.

The first cannula may have a first exterior surface and the second cannula may have a second exterior surface. The second exterior surface of the second cannula may be in sliding contact with the first exterior surface of the first cannula.

Optionally, the apparatus may include a sheath tube that is fixedly attached to the first cannula along the longitudinal extent of the first cannula. The sheath tube may have a guide lumen, wherein the second cannula is positioned in the guide lumen of the sheath tube for slidable movement within the guide lumen of the sheath tube.

In any of the embodiments, the second cannula may have an articulation joint interposed between the proximal end portion and the distal end portion. The distal end portion and the articulation joint may be extendable in a distal direction beyond the distal end of the first cannula. The second cannula may be articulated at the articulation joint by operation of the operator handle.

In any of the embodiments, the operator handle may be configured to rotate the second cannula relative to the first cannula.

In any of the embodiments, the apparatus may include a translation member having a first end and a second end. The first end is attached to the distal end portion of the second cannula and second end is attached to the operator handle.

In any of the embodiments, the operator handle may be configured to extend the second cannula relative to the first cannula, to retract the second cannula relative to the first cannula, and/or to rotate the second cannula relative to the first cannula.

In any of the embodiments, the apparatus may include an intravascular device received in the second lumen of the second cannula. The intravascular device has a distal working portion that extends distally from the distal end portion of the second cannula.

In any of the embodiments, the apparatus may include a guide wire located in the first lumen of the first cannula. The guide wire may be configured to project from each of the proximal end and the distal end of the first cannula.

In any of the embodiments, the apparatus may include a guide wire, an intravascular device, and a magnetic coupler. The guide wire may be located in the first lumen of the first cannula. The guide wire may be configured to project from the distal end of the first cannula. The intravascular device may be received in the second lumen of the second cannula. The intravascular device has a distal working portion that extends distally from the distal end portion of the second cannula. The magnetic coupler is configured to generate a passive magnetic bond between the guide wire and the distal working portion of the intravascular device.

Optionally, the passive magnetic bond may be broken when vibrational energy is applied to the intravascular device.

In any of the embodiments, the apparatus may include a guide wire and an intravascular device. The guide wire may be located in the first lumen of the first cannula. The guide wire may be configured to project from each of the proximal end and the distal end of the first cannula. The guide wire may have an attraction section that extends from the distal end of the first cannula. The intravascular device may be received in the second lumen of the second cannula. The intravascular device may have a distal working portion that extends distally from the distal end portion of the second cannula. The distal working portion has an attraction member. At least one of the attraction section and the attraction member has a magnet to generate a magnetic force to magnetically bond the distal working portion of the intravascular device to the attraction section of the guide wire, and, optionally, the other of the attraction section and the attraction member is a ferromagnetic material that is magnetically attracted to the magnet.

The attraction section may include a plurality of attraction elements spaced along a longitudinal extent of the guide wire, wherein each of the plurality of attraction elements is one of a magnet and a ferromagnetic material.

Optionally, the attraction section may include a plurality of annular bands spaced along a longitudinal extent of the guide wire, wherein each of the plurality of annular bands is one of a magnet and a ferromagnetic material.

In another form, the invention relates to an endovascular apparatus having a first cannula, a second cannula, a guide wire, an intravascular device, and a magnetic coupler. The first cannula has a proximal end, a distal end, and a first lumen. The second cannula has a proximal end portion, a distal end portion, and a second lumen. The guide wire is located in the first lumen of the first cannula. The guide wire is configured to project from the distal end of the first cannula. The intravascular device is received in the second lumen of the second cannula. The intravascular device has a distal working portion that extends distally from the distal end portion of the second cannula. The magnetic coupler is configured to generate a passive magnetic bond between the guide wire and the distal working portion of the intravascular device. The endovascular apparatus is configured to generate a passive magnetic bond between the guide wire and the distal working portion of the intravascular device, by means of the magnetic coupler.

The intravascular device may be configured to be coupled to an ultrasonic source to receive a vibrational wave and to transmit the vibrational wave to the distal working portion, and wherein the passive magnetic bond may be broken when vibrational energy is applied to the intravascular device.

In any of the embodiments, the apparatus may include an operator handle operably coupled to the second cannula. The operator handle may be configured to articulate the distal end portion of the second cannula relative to the first cannula.

In any of the embodiments, optionally, the apparatus may include an elongate sheath having a sheath lumen. The first cannula and the second cannula may be positioned in the sheath lumen of the elongate sheath. The second cannula is slidable relative to the first cannula within the sheath lumen of the elongate sheath.

Alternatively, the apparatus may include a sheath tube fixedly attached to the first cannula along the longitudinal extent of the first cannula. The sheath tube has a guide lumen, wherein the second cannula may be positioned in the guide lumen of the sheath tube for slidable movement within the guide lumen of the sheath tube.

In any of the embodiments, the second cannula may have an articulation joint interposed between the proximal end portion and the distal end portion. The distal end portion and the articulation joint may be extendable in a distal direction beyond the distal end of the first cannula. The second cannula may be articulated at the articulation joint.

In any of the embodiments, an operator handle may operably be coupled to the second cannula, the operator handle configured to articulate the distal end portion of the second cannula relative to the first cannula and/or to rotate (clockwise and/or counterclockwise) the second cannula relative to the first cannula and/or to selectively move the second cannula longitudinally relative to the first cannula.

In any of the embodiments, the apparatus may include a translation member having a first end and a second end. The first end is attached to the distal end portion of the second cannula and second end is attached to the operator handle.

In any of the embodiments, the operator handle may be configured to extend the second cannula relative to the first cannula, to retract the second cannula relative to the first cannula, and/or to rotate the second cannula relative to the first cannula.

In any of the embodiments, the apparatus may include a guide wire and an intravascular device. The guide wire may be located in the first lumen of the first cannula. The guide wire may be configured to project from each of the proximal end and the distal end of the first cannula. The guide wire may have an attraction section that extends from the distal end of the first cannula. The intravascular device may be received in the second lumen of the second cannula. The intravascular device may have a distal working portion that extends distally from the distal end portion of the second cannula. The distal working portion has an attraction member. At least one of the attraction section and the attraction member has a magnet to generate a magnetic force to magnetically bond the distal working portion of the intravascular device to the attraction section of the guide wire, and, optionally, the other of the attraction section and the attraction member is a ferromagnetic material that is magnetically attracted to the magnet.

The attraction section may include a plurality of attraction elements spaced along a longitudinal extent of the guide wire, wherein each of the plurality of attraction elements is one of a magnet and a ferromagnetic material.

Optionally, the attraction section may include a plurality of annular bands spaced along a longitudinal extent of the guide wire, wherein each of the plurality of annular bands is one of a magnet and a ferromagnetic material.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An endovascular apparatus, comprising:
a first cannula having a proximal end, a distal end, and a first lumen, wherein the first cannula has a longitudinal extent between the proximal end and the distal end;
a second cannula slidably coupled to the first cannula, the second cannula having a proximal end portion, a distal end portion, and a second lumen, the distal end portion being extendable in a distal direction beyond the distal end of the first cannula;
an operator handle operably coupled to the second cannula, the operator handle having a hub pivotably coupled to the second cannula, the hub configured to articulate the distal end portion of the second cannula relative to the first cannula; and
a sheath tube fixedly attached to the first cannula along the longitudinal extent, the sheath tube having a guide lumen, wherein the second cannula is positioned in the guide lumen of the sheath tube for slidable movement within the guide lumen of the sheath tube.

2. The apparatus of claim 1, comprising an elongate sheath having a sheath lumen, the first cannula and the second cannula being positioned in the sheath lumen of the elongate sheath, the second cannula being slidable relative to the first cannula within the sheath lumen of the elongate sheath.

3. The apparatus of claim 1, wherein the first cannula has a first exterior surface and the second cannula has a second exterior surface, the second cannula being slidably coupled to the first cannula with the second exterior surface of the second cannula being in sliding contact with the first exterior surface of the first cannula.

4. The apparatus of claim 1, wherein the second cannula has an articulation joint interposed between the proximal end portion and the distal end portion, the distal end portion and the articulation joint being extendable in a distal direction beyond the distal end of the first cannula, the second cannula being articulated at the articulation joint by operation of the operator handle.

5. The apparatus of claim 1, comprising a magnetic coupler configured to generate a passive magnetic bond between the first cannula and the second cannula.

6. An endovascular apparatus, comprising:
a first cannula having a proximal end, a distal end, and a first lumen;
a second cannula slidably coupled to the first cannula, the second cannula having a proximal end portion, a distal end portion, and a second lumen, the distal end portion being extendable in a distal direction beyond the distal end of the first cannula;
a guide wire located in the first lumen of the first cannula, the guide wire configured to project from the distal end of the first cannula;
an intravascular device received in the second lumen of the second cannula, the intravascular device having a distal working portion that extends distally from the distal end portion of the second cannula;
a magnetic coupler configured to generate a passive magnetic bond between the guide wire and the distal working portion of the intravascular device, the passive magnetic bond being broken when a vibrational energy is applied to the intravascular device; and
an operator handle operably coupled to the second cannula, the operator handle configured to articulate the distal end portion of the second cannula relative to the first cannula, wherein the operator handle is configured to rotate the second cannula relative to the first cannula.

7. The apparatus of claim 6, comprising a translation member having a first end and a second end, the first end being attached to the distal end portion of the second cannula and the second end being attached to the operator handle.

8. The apparatus of claim 6, wherein the operator handle is configured to extend the second cannula relative to the first cannula, to retract the second cannula relative to the first cannula, and to rotate the second cannula relative to the first cannula.

9. The apparatus of claim 6, comprising a guide wire located in the first lumen of the first cannula, the guide wire configured to project from each of the proximal end and the distal end of the first cannula.

10. The apparatus of claim 6, wherein:
the guide wire has an attraction section that extends from the distal end of the first cannula; and
the intravascular device has a distal working portion that extends distally from the distal end portion of the second cannula, the distal working portion having an attraction member; wherein
at least one of the attraction section and the attraction member has a magnet to generate a magnetic force to magnetically bond the distal working portion of the intravascular device to the attraction section of the guide wire, and the other of the attraction section and the attraction member is a ferromagnetic material that is magnetically attracted to the magnet.

11. The apparatus of claim 10, wherein the attraction section includes a plurality of attraction elements spaced along a longitudinal extent of the guide wire, wherein each of the plurality of attraction elements is one of a magnet and a ferromagnetic material.

12. The apparatus of claim 10, wherein the attraction section includes a plurality of annular bands spaced along a longitudinal extent of the guide wire, wherein each of the plurality of annular bands is one of a magnet and a ferromagnetic material.

13. An endovascular apparatus, comprising:
a first cannula having a proximal end, a distal end, and a first lumen wherein the first cannula has a longitudinal extent between the proximal end and the distal end;

a second cannula having a proximal end portion, a distal end portion, and a second lumen;

a guide wire located in the first lumen of the first cannula, the guide wire configured to project from the distal end of the first cannula;

a sheath tube fixedly attached to the first cannula along the longitudinal extent, the sheath tube having a guide lumen, wherein the second cannula is positioned in the guide lumen of the sheath tube for slidable movement within the guide lumen of the sheath tube;

an intravascular device received in the second lumen of the second cannula, the intravascular device having a distal working portion that extends distally from the distal end portion of the second cannula; and a magnetic coupler configured to generate a passive magnetic bond between the guide wire and the distal working portion of the intravascular device.

14. The apparatus of claim 13, wherein the intravascular device is configured to be coupled to an ultrasonic source to receive a vibrational wave and to transmit the vibrational wave to the distal working portion, and wherein the passive magnetic bond is broken when vibrational energy is applied to the intravascular device.

15. The apparatus of claim 13, comprising an elongate sheath having a sheath lumen, the first cannula and the second cannula being positioned in the sheath lumen of the elongate sheath, the second cannula being slidable relative to the first cannula within the sheath lumen of the elongate sheath.

16. The apparatus of claim 13, wherein the second cannula has an articulation joint interposed between the proximal end portion and the distal end portion, the distal end portion and the articulation joint being extendable in a distal direction beyond the distal end of the first cannula, the second cannula being articulated at the articulation joint.

17. The apparatus of claim 16, comprising an operator handle operably coupled to the second cannula, the operator handle configured to articulate the distal end portion of the second cannula relative to the first cannula.

* * * * *